United States Patent [19]

Stefanadis et al.

[11] Patent Number: 5,342,300
[45] Date of Patent: Aug. 30, 1994

[54] STEERABLE STENT CATHETER

[76] Inventors: Christodoulos I. Stefanadis, Tepeleniou 9, Palaio Psihiko, Athens 15452; Pavlos K. Tovtouzas, Karaoli & Thimitriou, 24 Cholargos, Athens 15561, both of Greece

[21] Appl. No.: 30,674

[22] Filed: Mar. 12, 1993

[30] Foreign Application Priority Data

Mar. 13, 1992 [GR] Greece .................. 920100104

[51] Int. Cl.$^5$ ............................ A61M 37/00
[52] U.S. Cl. ......................... 604/95; 606/198
[58] Field of Search ............ 604/95, 280, 281, 282, 604/283; 606/198, 195, 194, 192, 191, 200

[56] References Cited

U.S. PATENT DOCUMENTS

| 4,769,006 | 9/1988 | Papantonakos | 604/95 |
| 5,025,799 | 6/1991 | Wilson | 604/95 X |
| 5,125,395 | 6/1992 | Adair | 604/95 X |
| 5,201,901 | 4/1993 | Harada et al. | 606/198 |

*Primary Examiner*—John D. Yasko
*Attorney, Agent, or Firm*—Olson & Hierl, Ltd.

[57] ABSTRACT

Distal end of a vascular catheter is provided with diameter whose outside can be adjusted by external manipulations. Contracted the spirals are in contact with the outer surface of the catheter wall, thus allowing easy insertion of the catheter device in the region of the dissected vessel wall. When expanded to the desired diameter in contact with the vessel wall, the spirals support the dissected flap against the vessel wall while allowing blood flow through the lumen, the present endoprosthesis can be deployed with simple percutaneous vascular catheterization and can be readily removed after the desired therapeutic effect has been achieved. The endoprosthesis is useful in cases of acute wall dissection of blood vessels such as the aorta and the coronary arteries.

2 Claims, 2 Drawing Sheets

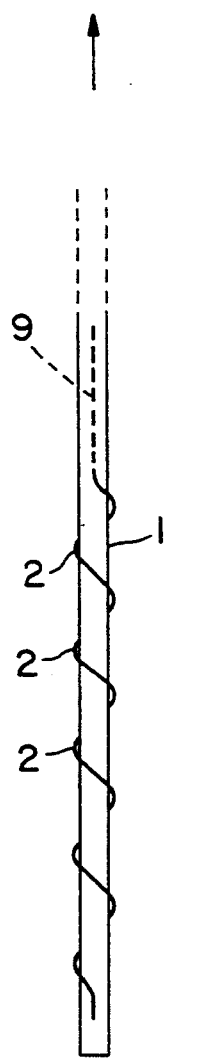
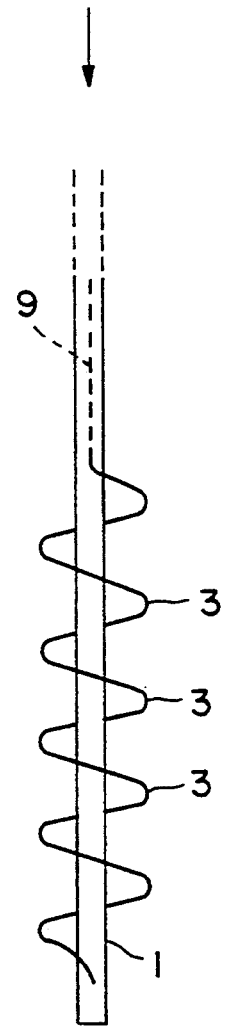
FIG. 1     FIG. 2
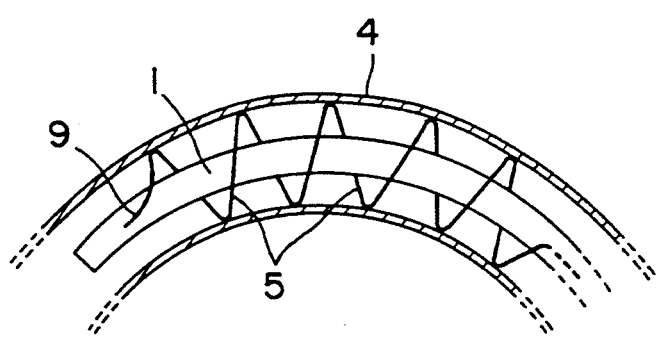
FIG. 3

STEERABLE STENT CATHETER

TECHNICAL FIELD

The invention concerns an endoprosthesis for the support of a blood vessel wall.

BACKGROUND OF THE INVENTION

The acute dissection of a blood vessel wall can threaten a patient's life, especially in (1) acute dissection of wall of the coronary arteries, as a complication of angioplasty, and (2) in acute dissecting aneurysm of the aorta. In the former case, the flap of the intima inhibits the distal flow of blood, resulting in myocardial infarction. To treat this complication, the patient is operated urgently for coronary artery bypass surgery, which is associated with high perioperative mortality. Adjunctively and mainly as a "bridge" to the operating theatre, certain types of balloon catheters (autoperfusion catheters) are used. These catheters, through special apertures, permit an amount of blood to flow to the periphery, while supporting the flap against the vessel wall during the time they are situated in the area of the lesion. Another way to treat the acute dissection of the coronary arteries, without surgical intervention, is the permanent placement of endoprostheses (stents), made of metal in most of the cases, which in their expanded form support the flap and permit the flow of blood through the lumen. Stents are, however, associated with high acute thrombosis (4–20%) and restenosis (approximately 30%) rate. As far as the acute dissection of the aorta is concerned, the only relatively effective way of treatment is the surgical placement of a graft. However, such intervention is associated with high perioperative mortality, especially if the aneurysm is extensive or if it involves vital vessels.

SUMMARY OF THE INVENTION

The present invention bypasses the serious disadvantages of the above mentioned methods and provides an effective solution to the problem that acute dissection poses. The present invention permits the rapid treatment, without any loss of time, of the problem by means of a simple percutaneous vascular catheterization, thereby preventing prolonged ischemia and a progression of dissection with time. Also, the present invention makes it possible for the dissected flap to become attached to the vessel wall, resulting thus in a permanent treatment. Accordingly, the presently contemplated manner of treatment is superior to surgical treatment because: (1) the elapsed time to the completion of the therapeutic intervention, directly related to mortality, is reduced, and (2) dangers that may arise from an urgent and severe operation that often is performed under extracoproreal circulation are avoided. It is emphasized that, with regard to dissecting aneurysms of the aorta, heretofore no alternative to surgical intervention has been proposed. When compared to conventional stents, the present invention is not associated with the complications that arise from a prolonged presence of other endoprostheses in the interior of the vessel, because the present stent is removed when the desired therapeutic result has been achieved. Also, there are no disadvantages as far as effectiveness supporting the dissected flap and restoring antegrade flow are concerned.

The present invention provides a steerable stent catheter that is eminently well suited for transluminal endoprosthesis. This catheter has an elongated, flexible, hollow shaft equipped with a steering wire for the shaft which wire serves a dual function. More particularly, the steering wire has a coiled portion of variable diameter that is adjustable in size to support a contiguous portion of a blood vessel wall. To that end, the steering wire extends along the hollow catheter shaft, has a coiled distal portion wrapped around the distal portion of the shaft, and the distal end of the steering wire is secured to the distal end portion of the shaft. A forwardly movement of the steering wire along the longitudinal axis of the shaft increases the outside diameter of the coiled wire portion while a rearwardly movement of the wire along the longitudinal axis of the shaft reduces the outside diameter of the coiled wire portion by wrapping the steering wire about the outer surface of the catheter shaft and in contact therewith.

Additionally, in the event the attachment of the dissected walls is not achieved, the stent catheter device of this invention serves as a "bridge" to the operating theatre. Specifically, with regard to dissecting aneurysms of the aorta, the device of this invention offers the only solution for the restoration of the blood flow, and the prevention of the progression of the dissection with time, during the critical time period that elapses until the patient is operated upon. With regard to coronary dissection, when compared to the existing conventional alternatives of temporary treatment of the problem, the present device is superior in that (1) it offers better conductance, (2) the flexibility of the device permits placement in dissection along vessel curvatures, (3) it has the ability to be in complete contact with the vessel wall of tapered arteries, due to the fact that along the length of the device, the spirals can have different diameter the one from the other.

BRIEF DESCRIPTION OF THE DRAWINGS

FIG. 1 shown the distal part of a catheter embodying the present invention with wire spirals in their completely contracted form;

FIG. 2 shows the distal part of the same catheter as in FIG. 1, but with the spirals in their expanded form;

FIG. 3 shows the distal part of a catheter of this invention with wire spirals in their expanded form along a curved portion of a blood vessel;

DESCRIPTION OF THE PREFERRED EMBODIMENT

The present invention is described in detail below with reference to the aforementioned drawings which illustrate one specific embodiment.

Figure 4:
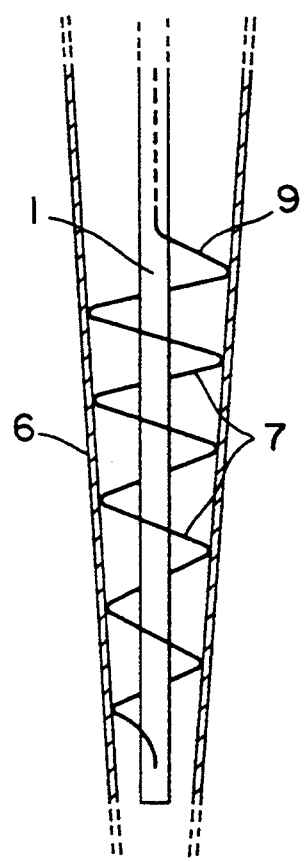
FIG. 4 shows the distal part of a catheter of this invention with wire spirals in their expanded form along a tapered portion of a vessel.
Figure 5:
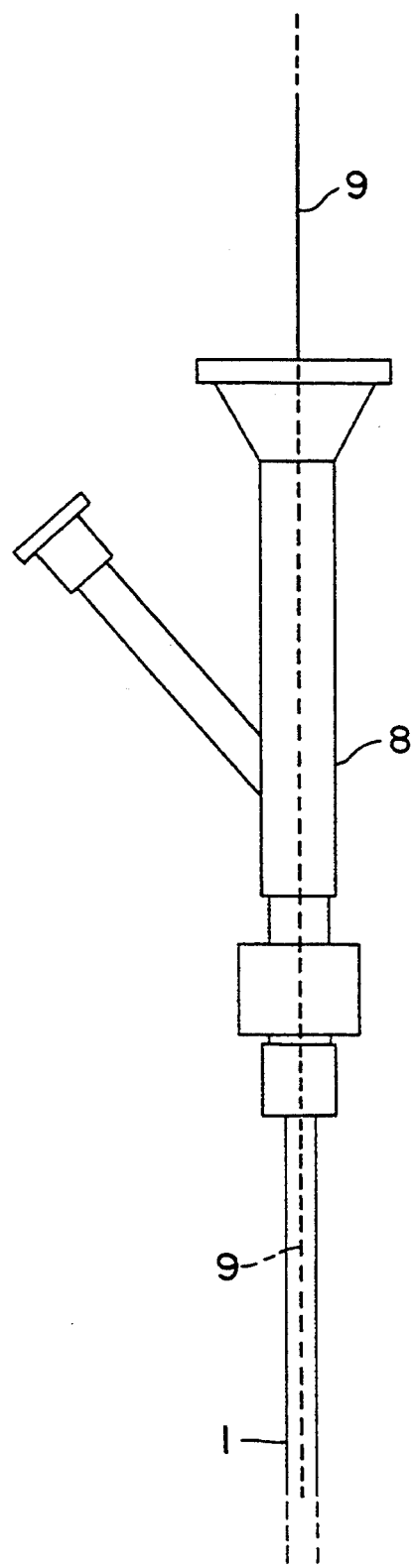
FIG. 5 shows the proximal part of a catheter provided with a steering system that also can provide a stent at the distal part thereof as shown in FIGS. 1-4, above.

The drawings illustrate the temporary transluminal endoprostheses for the support of the vessel wall, which consists of a vascular catheter that has in its proximal part (8) a steering arm or wire (9) made of stainless steel or material with similar elastic properties as regards twisting and bending. This steering arm or wire passes through the lumen of the catheter shaft and emerges (1) a short distance from the distal end of catheter shaft (1) where it forms spirals (2). The distal end region of the arm or wire (9) is attached to the distal end of the catheter as shown in FIG. 1. When the arm or wire (9), by external manipulations, is retracted, the spirals (2) are in complete contact with the outer surface of the catheter shaft (1), allowing thus the easy insertion of the device in the region of the lesion. With the advancement of the arm wire (9) along catheter shaft 1, again by external manipulations, the diameter of the spirals (2) increases, as shown in FIG. 2 for arm or wire turns (3), until the diameter of the turns coincides with the diameter of the vessel wall so that the dissected flap is held in complete contact with the vessel wall. The device is flexible and can be placed along vessel curvatures such as curvature (4) shown in FIG. 3 where arm or wire turns 5 are contiguous with the wall of the vessel. Additionally, the spirals of an individual device embodying this invention can acquire different diameter turns, one from the other, as shown in FIG. 4 where turns (7) have a progressively smaller outside diameter toward the distal end of shaft (1) so as to abut the inner wall of tapered vessel (6) and in complete contact with the vessel wall along the tapered portion of vessels (6).

When the present transluminal endoprosthesis is positioned in the region of the blood vessel where a stent is desired, the steering wire 9 is at its rearwardmost extension, and the coiled region of the wire abuts the outer surface of the enveloped catheter shaft as can be seen in FIG. 1. Movement of the steering wire 9 forwardly, i.e., in the direction of the arrow in FIG. 2, expands the outer diameter of the coiled wire portion. The expansion of the outer diameter continues until the individual spirals of the coiled wire portion abut the blood vessel wall as shown in FIGS. 3 and 4. Inasmuch as steering wire 9 is a continuous strand, the individual spirals or coils need not have the same diameter but can be readily adapted to various diameters as determined by the inside dimension of the region where the stent is to be placed. To remove the stent, steering wire 9 is first moved rearwardly to collapse the coiled region about the catheter shaft, and the catheter is then withdrawn from the patient.

The foregoing discussion and the accompanying drawings are intended to be illustrative and are not to be taken as limiting. Still other variations within the spirit and scope of this invention are possible and will readily present themselves to those skilled in the art.

We claim:

1. A vascular catheter suitable for transluminal endoprosthesis which comprises:
    an elongated, flexible, hollow shaft; and
    a steering wire for said shaft;
    said steering wire extending along the hollow shaft and being secured to the distal end portion of the shaft, a distal portion of the steering wire being coiled around the shaft so that a forwardly movement of the steering wire along the longitudinal axis of the shaft increases the outside diameter of the coiled wire portion and a rearwardly movement of the wire along the longitudinal axis of the shaft reduces the outside diameter of the coiled wire portion; said steering wire having a coiled portion and a straight portion, and the straight portion being situated inside the hollow shaft.

2. The vascular catheter in accordance with claim 1 wherein the steering wire is made of stainless steel.

* * * * *